United States Patent [19]

Makarevich et al.

[11] 4,175,078
[45] Nov. 20, 1979

[54] CARDENOLIDE AND BUFADIENOLIDE DERIVATIVES OF AJMALINE AND PROCESS FOR PRODUCING SAME

[75] Inventors: Ivan F. Makarevich; Yaroslav I. Khadzhai; Valeria V. Pavlova; Anastasia V. Nikolaeva, all of Kharkov, U.S.S.R.

[73] Assignee: Kharkovsky Naucho-Issledovatelsky Khimfo-Farmatsevtiches-Ky Institut, Kharkov, U.S.S.R.

[21] Appl. No.: 924,922

[22] Filed: Jul. 14, 1978

Related U.S. Application Data

[63] Continuation-in-part of Ser. No. 880,694, Feb. 22, 1978, abandoned, which is a continuation of Ser. No. 735,211, Oct. 22, 1976, abandoned.

[51] Int. Cl.$^2$ ............................................. C07J 19/00
[52] U.S. Cl. ............................... 260/239.57; 424/241
[58] Field of Search ...................................... 260/239.57

[56] References Cited

U.S. PATENT DOCUMENTS 3,886,268   5/1975   Halpern ................................ 424/243

Primary Examiner—Ethel G. Love
Attorney, Agent, or Firm—Haseltine, Lake & Waters

[57] ABSTRACT

According to the invention, the novel substances are the cardenolide and bufadienolide derivatives of ajmaline of the general formula

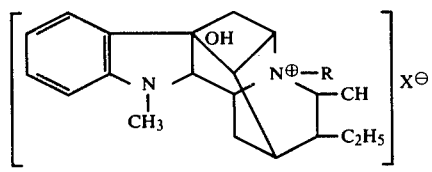

wherein R is cardenolide or bufadienolide of the general formula

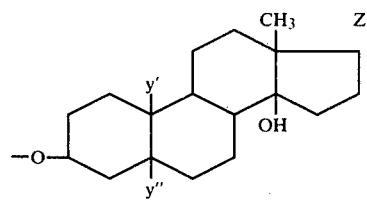

Z is an unsaturated five-member or six-member lactone ring of the general formula

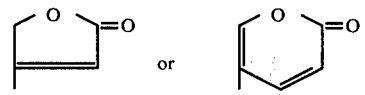

y' is a radical —CH$_3$, or —CHO;
y" is H or OH,
X is a halogen.

According to the present invention, the process for producing the cardenolide or bufadienolide derivatives of ajmaline resides in that cardenolide or bufadienolide is reacted with acid halides in a medium of an organic solvent, which does not react with organic acid anhydrides, at a temperature of −10° to +25° C., and added to the thus-obtained halide of cardenolide or bufadienolide is ajmaline in a medium of said organic solvent, followed by isolation of the end product.

The proposed novel derivatives of ajmaline are capable of producing two therapeutically important effects: relieving cardiac arrhythmia and tonicizing the cardiac activity. They find application in medicine as the active principle of medicinal preparations for treatment and prophylaxis of severe forms of cardiac diseases, such as myocardial infarction, arrhythmia that aggravates hypertensive disease, cardiosclerosis, chronic coronary insufficiency, rheumatism, infectious myocarditis, mitral valve disease and a number of other grave and prevalent cardiac diseases.

7 Claims, No Drawings

CARDENOLIDE AND BUFADIENOLIDE DERIVATIVES OF AJMALINE AND PROCESS FOR PRODUCING SAME

The present application is a continuation-in-part of Ser. No. 880,694, filed Feb. 22, 1978, which is a continuation of application Ser. No. 735,211 filed on Oct. 22, 1976, both abandoned.

The present invention relates to novel substances—cardenolide and bufadienolide derivatives of ajmaline and a process for the production thereof.

FIELD OF APPLICATION

The proposed novel derivatives of ajmaline produce two important therapeutic effects—an ability to relieve cardiac arrhythmia and tonicize the cardiac activity. They find application in medicine as the active principle of medicinal preparations for therapy and prophylaxis of severe forms of cardiac diseases such as myocardial infarction, arrhythmia, diseases that aggravate hypertension, cardiosclerosis, chronic coronary insufficiency, rheumatism, infectious myocarditis, mitral valve disease, and a number of other grave and prevalent diseases.

BRIEF DESCRIPTION OF THE INVENTION

The novel substances—cardenolide and bufadienolide derivatives of ajmaline have the following general formula:

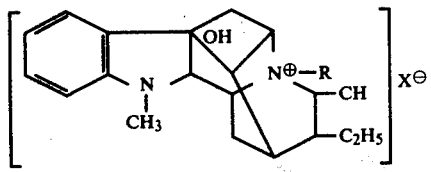

wherein
R is cardenolide or bufadienolide of the general formula:

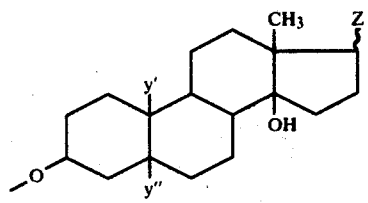

Z is an unsaturated five-membered lactone ring of the general formula

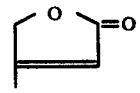

or an unsaturated six-membered lactone ring of the general formula

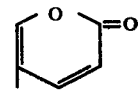

y' is a radical —$CH_3$ or —CHO;
y" is H or OH;
X is a halogen.

The following substances have the highest pharmacological activity:

strophanthidin-3,O-acetyl-2'-N($\beta$)-ajmaline-bromide of the following formula:

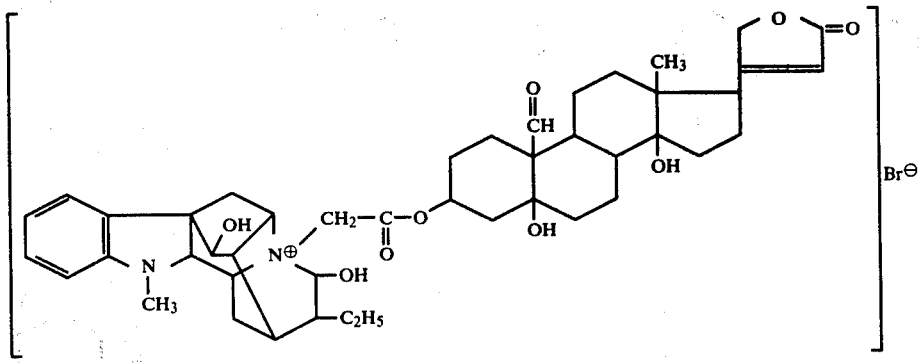

hellebrigenine-3-O-acetyl-2'-N(b)-ajmaline-bromide of the following formula:

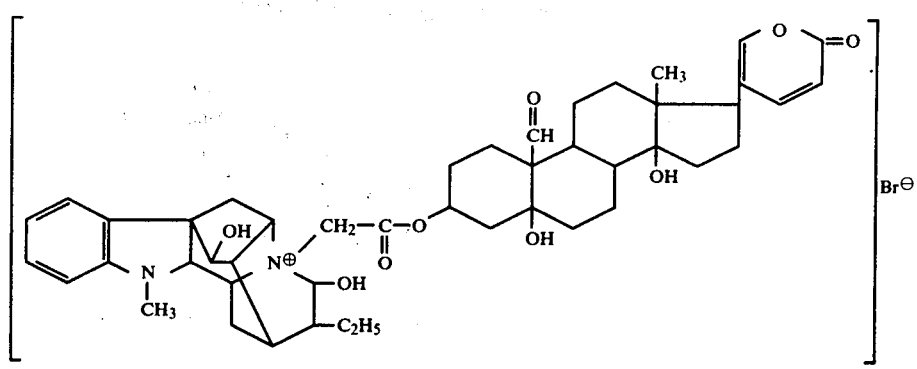
17 β-H-strophanthidin-3-O-acetyl-2$^I$-N-(b)-ajmaline-bromide;
strophanthidin-3-O-acetyl-2$^I$-N(b)-ajmaline-chloride
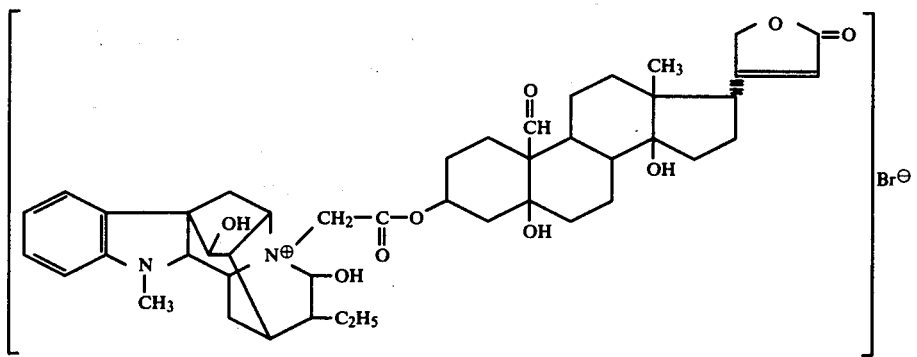
digitoxigenin-3-O-acetyl-2$^I$-N(b)-ajmaline-bromide
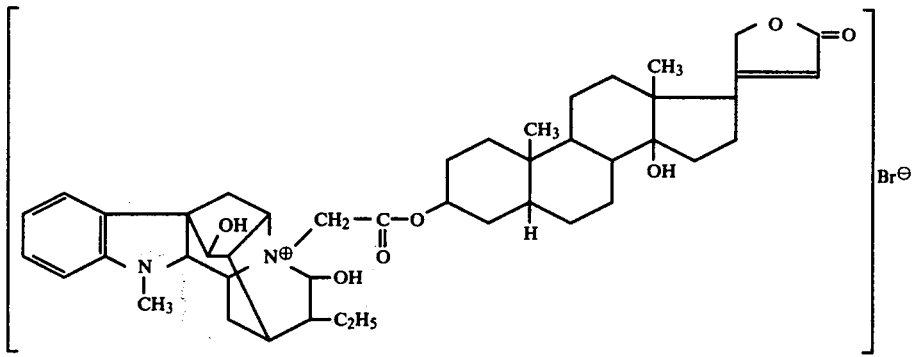
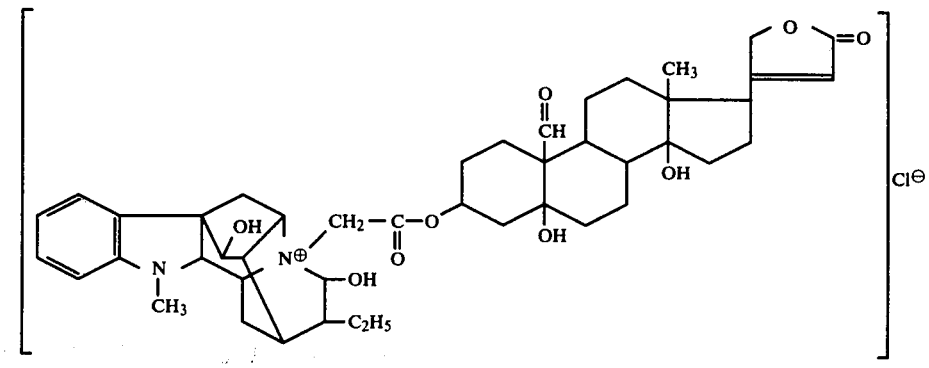

BRIEF DESCRIPTION OF THE INVENTION

Studies into the physico-chemical properties of the novel compounds have been carried out to show the following results.

Cardenolide and bufadienolide derivatives of ajmaline are white crystalline powders soluble in alcohol, pyridine, and dimethylformamide and are optically active.

They are capable of yielding reactions both for cardenolides (Légal's, Raymond's, Kedtze's) and for ajmaline (they develop red coloration with concentrated nitric acid, or blue fluorescence after having been irradiated with nonfiltered UV rays).

The reaction for Br⁻ is positive. Each of the compounds possesses its own molecular and structural formula, melting point and specific rotation.

Thus, for example, strophanthidin-3-O-acetyl-2$^I$-N(b)-ajmaline-bromide has a melting point of 210° to 212° C.;

[α]$_D$= +41.5° (concentration of 2.0 in a pyridine solution);

[M]$_D$= +353° (in pyridine); empirical formula, $C_{45}H_{59}O_9N_2Br$, its structural formula being:

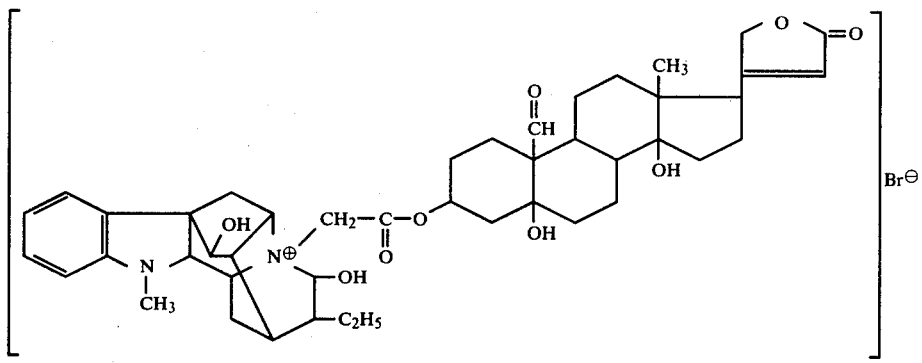

Hellebrigenine-3-O-acetyl-2$^I$-N(b)-ajmaline-bromide has a melting point of 238° to 241° C.; [α]$_D$= +28.3° (concentration of 1.0 in a pyridine solution); [M]$_D$= +244° (in pyridine); empirical formula, $C_{46}H_{59}O_9N_2Br$, its structural formula being

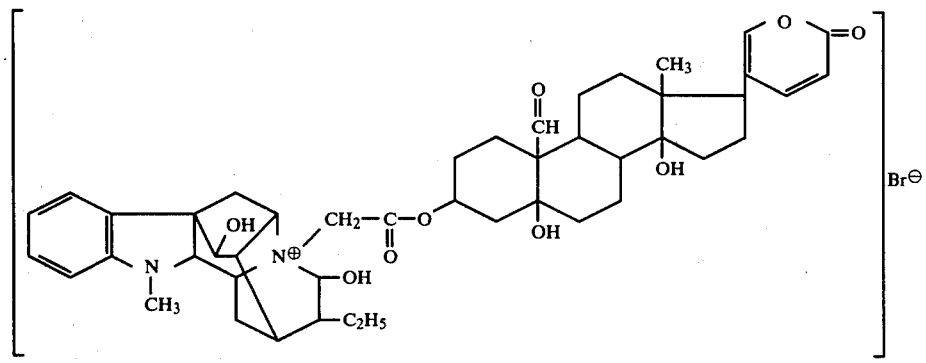

Digitoxigenin-3-O-acetyl-2$^I$-N(b)-ajmaline-bromide has a melting point of 215° to 218° C.; [α]$_D$= +58.0° (concentration of 3.0 in an ethyl alcohol solution); [M]$_D$=477°±24° (in ethanol); empirical formula $C_{45}H_{61}O_7N_2Br$, its structural formula being

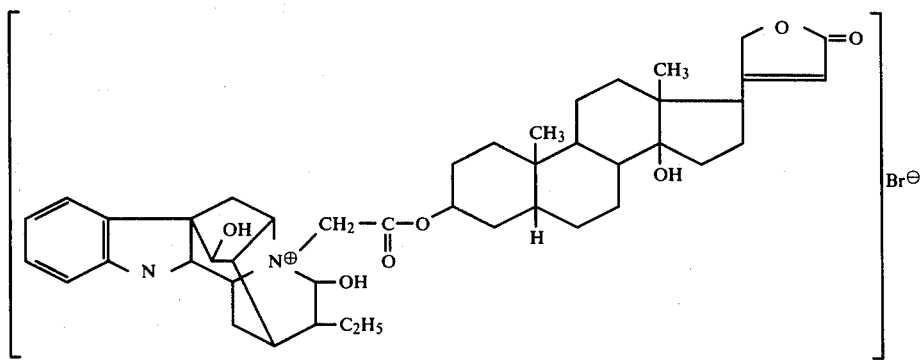

17β-H-strophanthidin-3-O-acetyl-2$^I$-N(b)-ajmaline-bromide has a melting point of 217°to 220° C.;

$[\alpha]_D = +71.1°$ C. (concentration of 3.0 in an ethyl alcohol solution); $[M]_D = +605.8 \pm 27°$ (in ethanol); empirical formula $C_{45}H_{59}O_9N_2Br$, its structural formula being

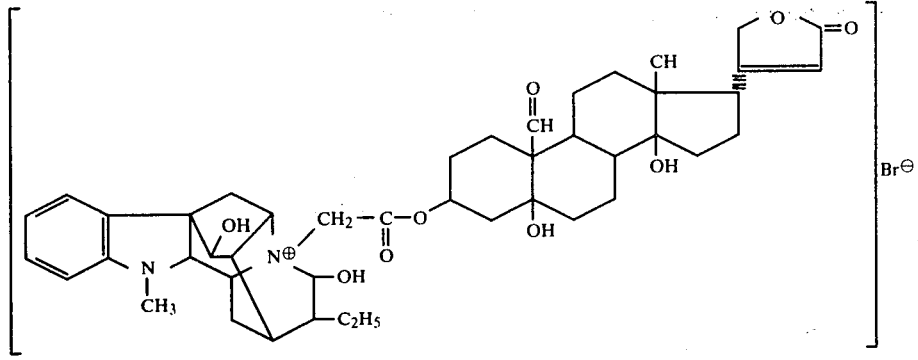

Strophanthidin-3-O-acetyl-$2^I$-N(b)-ajmaline-bromide has a melting point of 250° to 253° C.; $[\alpha]_D = +43° \pm 2°$ (concentration of 1.0 in a pyridine solution); $[M]_D = +347° \pm 16°$ (in pyridine); empirical formula $C_{45}H_{59}O_9N_2Cl$, its structural formula being

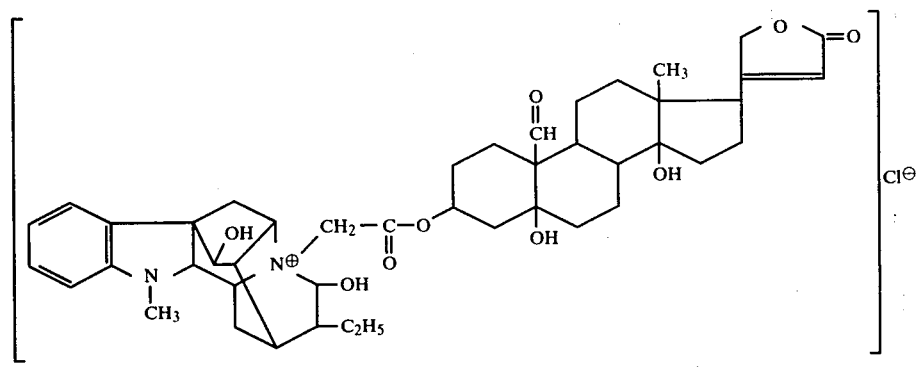

The above-mentioned novel compounds have been studied for pharmacological activity.

The antiarrhythmic activity of the agents was determined on the aconitine-, calcium- and strophanthidin-induced models in rats. Depending on the peculiarities of an experimental model, the prophylactic antiarrhythmic and arrhythmia-arresting effect of the agents was the subject of studies.

It is established that when injected intravenously in a dose of 10 mg/kg the proposed compounds produce a prophylactic antiarrhythmic effect causing restoration of the cardiac rhythm, on an average, within $17 \pm 2.5$ minutes as against 1 to 1.5 hour in the control experiment. Said effect is similar to that of ajmaline when injected intraperitoneally. When administered against a background of the already developed aconitine-induced arrhythmia the cardenolide and bufadienolide derivatives of ajmaline in a dose of 2 to 10 mg/kg are found to produce an arresting effect in 70 to 80% of the cases.

For example, when injected intravenously in a dose of 10 mg/kg strophanthidin-3-O-acetyl-$2^I$-N(b)-ajmaline-bromide produces a prophylactic antiarryhythmic effect thus causing the cardiac rhythm to restore on an average of $17 \pm 2.5$ minutes as against 1 to 1.5 hour in the control experiment; when injected in a dose of 5 to 10 mg/kg against a background of the already developed aconitine-induced arrhythmia it produces an arresting effect in 77% of the cases.

The prophylactic effect produced upon the calcium-chloride-induced ventricular fibrillation was tested in experiments on rats. It was found that the proposed substances in a dose of 2 mg/kg increase the rate of survival of the animals by 50% as compared to 17% in the control group. In a dose of 5 mg/kg the preparation prevents the development of ventricular fibrillation in 82% of the cases. When given in this dose the substances feature approximately the same antiarrhythmic activity as ajmaline.

For example, in experiments on rats strophanthidin-3-O-acetyl-$2^1$-N(b)-ajmaline-bromide in a dose of 2 mg/kg increases the rate of survival of the animals by 50% as compared to 17% in the control group, and when given in a dose of 5 mg/kg the preparation prevents the development of ventricular fibrillation in 82% of the cases.

The prophylactic effect upon the G-strophanthidin-induced cardiac arrhythmia was studied by intravenous injections of the substances in a dose of 3 mg/kg, the development of the strophanthin arrythmia being modified. The duration of the latter is much shortened. The rate of the animals' survival rises to 67% as against 30% in the control group.

Investigation into the cardiotonic activity was carried out in the following manner. In the first run of experiments on guinea pigs there was determined the biological potency of the preparation strophanthidin-3-O-acetyl-$2^1$-N(b)-ajmaline-bromide under the monitoring of ECG according to the techniques approved by the State Pharmacopoeia of the USSR. The following runs dealt with the study of the effects of the above-mentioned preparation on the cardiac activity of frogs and on isolated hearts of rabbits and cats.

When studying the biological potency of the proposed agents it was established that a continuous injection of a 0.1% solution of the proposed substances at a rate of 1 ml/min into the jugular vein of guinea pigs inflicted death upon the animals on an average within 7.5 minutes. For example, a continuous injection of a 0.1% solution of strophanthidin-3-O-acetyl-2¹-N(b)-ajmaline-bromide into the jugular vein of guinea pigs at a rate of 1 ml/min causes the death of the animals on an average within 7.5 minutes.

The median lethal dose is 13±1.0 mg/kg. After the cardiac arrest the ventricles remain contracted and the auricles are in the state of plethora which is characteristic of the effect produced by cardiac glycosides.

The biological potency of digitoxigenin-3-O-acetyl-2¹-N(b)-ajmaline-bromide was studied on guinea pigs. It was established that a continuous injection into the jugular vein of guinea pigs of a 0.02% solution of the preparation at a rate of 1 ml/min causes the death of the animals on an average within 20 minutes. The median lethal dose is 8.9±0.9 mg/kg as against 4.1±0.23 mg/kg for strophanthidin.

The effects of the progressing doses of the proposed agents injected into the cardiac ventricle, upon the cardiac activity were studied in experiments on frogs, said doses ranging from 0.1 to 0.2 ml with a concentration of 0.25 to 0.05 percent by weight. For instance, investigation into the effects of the progressing doses of strophanthidin-3-O-acetyl-2¹-N(b)-ajmaline-bromide in the form of 0.25 to 0.05 wt.% solutions in amounts of 0.1 to 0.2 ml has shown that the substance causes the systolic cardiac arrest and is approximately five times less potent than strophanthidin K.

When determining the biological potency of frogs it was established that 17-β-H-strophanthidin-3-O-acetyl-2¹-N(b)-ajmaline-bromide in doses of 0.01 mg does not cause the systolic cardiac arrest as compared to strophanthidin. In large doses the biological potency of the preparation is considerably lower than that of other derivatives of this group of compounds studied previously.

In experiments on isolated hearts of rabbit and cat using the Langendorf technique it was found that the application of the cardenolide and bufadienolide derivatives of ajmaline increases the amplitude of cardiac systole in a greater degree as compared to strophanthidin (3 times as against 1.7, respectively, when taken in equimolar doses).

Strophanthidin-3-O-acetyl-2¹-N(b)-ajmaline-bromide increases the amplitude of cardiac systole to a greater extent than strophanthidin (3 times as against 1.7 times, respectively).

The effect of the proposed substances on the cardiac electrical activity and the arterial pressure was studied.

In this case the ECG taken from intact cats showed that the proposed agents cause an increase of the P-Q interval by 12 to 33% which is indicative of a delayed atrioventricular conduction and pulse retardation, the R-R interval becoming higher.

Thus, strophanthidin-3-O-acetyl-2'-N(b)-ajmaline-bromide causes an increase of the P-Q interval by 12-33%, the R-R interval becoming higher by 20%.

When the dose increases a broadening of the QRS complex is observed which shows a pronounced delay of the intraventricular condition. Injection of high doses of the preparation was followed in some cases by a diminished voltage of the wave P till its complete disappearance, as well as a deepening of the wave S.

The effects of the proposed substances on the artirial pressure was also studied. In acute experiments on cats involving the recording of the blood pressure in the carotid artery no substantial change in the arterial pressure was observed. Upon administration of toxic doses of the preparation to the animals a drop in the pressure is observed. A sharp depressor effect is accounted for by disturbed cardiac activity, i.e. a negative inotropic effect and disorder of the cardiac rhythm.

Investigations have also been carried out to determine the antiarrhythmic activity of the bufadienolide derivatives of ajmaline.

The biological potency of aimaline-3-O-acetyl-2¹-N(b)-ajmaline-bromide has been studied in experiments on intact rats in which arrhythmia has been induced by administration of aconitine or calcium chloride. A total of 46 albino rats of both sexes were used in the experiments, each animal weighing 130 to 230 g.

In intact rats (8 animals) the effects of the preparation on the bioelectric cardiac activity have been determined.

The antiarrhythmic activity of hellebrigenine-3-O-acetyl-2¹-N(b)-ajmaline-bromide has been studied on models of arrhythmia induced by calcium chloride or aconitine.

Depending on the specific features of an experimental model either prophylactic or arrhythmia arresting effect were studied. The preparation was injected in a dose of 2 mg/kg 10 minutes before injection of aconitine in rats. The dose of the preparation was selected on the basis of preliminary studies.

The ECG indices were taken from all the animals. Administration of hellebrigenine-3-O-acetyl-2¹-N(b)-ajmaline-bromide in the form of a 0.05% solution in a dose of 2 mg/kg at a rate of 1 ml/min results in 2 to 5 minutes in a change in the ECG indices—in an increase in the intervals and waves R-R, P-Q, and R. The interval R-R increases in 7 out of 8 rats by 33±6.26%. The increase in the interval R-R is representative of a retardation of the cardiac rhythm.

As the experiments have shown the interval P-Q (the atrioventricular conduction index) lengthens by 25±2.4% in half the test animals. In addition, upon the administration of the preparation an increase in the wave R by 45±7.5% is observed in all the animals. The model of ventricular fibrillation has been provoked in 12 rats by intravenous injection of calcium chloride in a dose of 20 mg/kg of a 10% solution. As shown by control tests, injection of calcium chloride causes ventricular fibrillation and inflicts death upon 10 animals out of 12, most of the animals dying 1 to 3 minutes after the injection of the preparation. The survived animals have been found to develop a drastically pronounced bradycardia.

Preliminary intravenous injection into eight rats of hellebrigenine-3-O-acetyl-2¹-N(b)-ajmaline-bromide resulted in the death of one animal only, i.e., the death rate was 12% as compared to 83% in the control experiment.

Preliminary injection of one of the proposed preparations in a dose of 5 mg/kg increased the percentage of survival of the animals to 62 in the case of digitoxigenin-3-O-acetyl-2¹-N(b)-ajmaline-bromide and to 55% in the case of 17-β-H-strophanthidin-3-O-acetyl-2¹-N(b)-ajmaline-bromide as against 21% in the control experiment. The percentage of survival in the group of rats to which ajmaline had been administered was 86.

Thus, in this model of arrhythmia digitoxigenin-3-O-acetyl-2¹-N(b)-ajmaline-bromide is more active than 17 β-H-strophanthidin-3-O-acetyl-2¹-N(b)-ajmaline-bromide and is inferior to ajmaline as regards the force of action.

Aconitine in the experiment disturbs almost all the cardinal functions of the heart: suppresses the automatism of the sinoauricular node and enhances excitability while contributing to the origination of numerous heterotropic stimulation foci. Aconitine was injected in a dose of 30 mg/kg. Out of 26 animals 19 were given aconitine alone and served as the control. In the control experiments, 2 to 4 minutes after aconitine administration cardiac arrhythmia and changes in the ECG indices develop; ventricular extrasystoles appear first sporadically, then in clusters. The ventricular rhythm thus set on turns into ventricular fibrillation, while atrioventricular conduction deranges concurrently. The arrhythmia lasts 87.3±7.2 minutes. The preliminary introduction of hellebrigenine-3-O-acetyl-2¹-N(b)-ajmaline-bromide in a dose of 2 mg/kg causes restoration of the cardiac rhythm, the duration of arrhythmia being reduced to 38.0±8.8 minutes.

The study of toxicity of the above-mentioned substances was carried out on mice and rats by various methods of their introduction into the organisms.

In experiments on mice involving intraperitoneal administration it has been established that the cardenolide and bufadienolide derivatives of ajmaline in therapeutic doses practically do not affect the behavior of the animals, whereas higher doses render the animals less mobile and less responsive to painful stimuli. Further increase of the doses results in the loss of righting reflex by the mice and in almost zero response to painful stimulus. Part of the animals die in 10 to 15 minutes. The $LD_{50}$ for the proposed agents is 430 to 464.5 mg/kg, while that for ajmaline is 130 mg/kg, and for quinidine—135 mg/kg.

Intraperitoneal injection of strophanthidin-3-O-acetyl-2¹-N(b)-ajmaline-bromide in experiments on mice practically does not affect the behavior of the animals. Upon administration of doses of 63 to 100 mg/kg the animals become less motile and less responsive to painful stimuli. Upon further increase of the dosage the animals lose righting reflex and their response to painful stimuli approximates zero. Part of the animals die in 10 to 15 minutes. The $LD_{50}$ for the proposed substances is 446.7 (430.0 to 464.5) mg/kg, while that for ajmaline is 130 mg/kg and for quinidine, 135 mg/kg.

The acute toxicity of digitoxigenin-3-O-acetyl-2¹-N(b)-ajmaline-bromide as compared with ajmaline was determined in experiments on 94 mice of both sexes, each weighing 17 to 20 g, by means of intraperitoneal injection of the preparation.

The study of the acute toxicity on mice has shown that the $LD_{50}$ of digitoxigenin-3-O-acetyl-2¹-N(b)-ajmaline-bromide is 743 (832–931) mg/kg. As regards the acute toxicity this preparation is five times less toxic than ajmaline for which the $LD_{50}$ is 142 (171–117) mg/kg.

Intravenous injection in experiments on rats has shown that the higher doses of the preparation produce similar phenomena, the median lethal dose being 175±6.8 mg/kg.

According to the invention, the processes for producing cardenolide and bufadienolide derivatives of ajmaline resides in that cardenolide or bufadienolide is made to react with acid halides in a medium of an organic solvent at a temperature of −10° to +5° C., whereupon added to the thus-obtained halide of cardenolide or bufadienolide is ajmaline in a medium of an organic solvent, followed by isolation of the end product.

Monobromo-acetyl-bromide is preferably used as an acid halide.

The process for producing cardenolide and bufadienolide derivatives of ajmaline, according to the invention, is carried out in the following preferred manner.

Cardenolide or bufadienolide is made to react with a halogen-containing reactant at a temperature of −10° to +25° C. in a medium of an organic solvent, such as monobromoacetyl-bromide.

For example, if the original stock is strophanthidin, the reaction runs the following course:

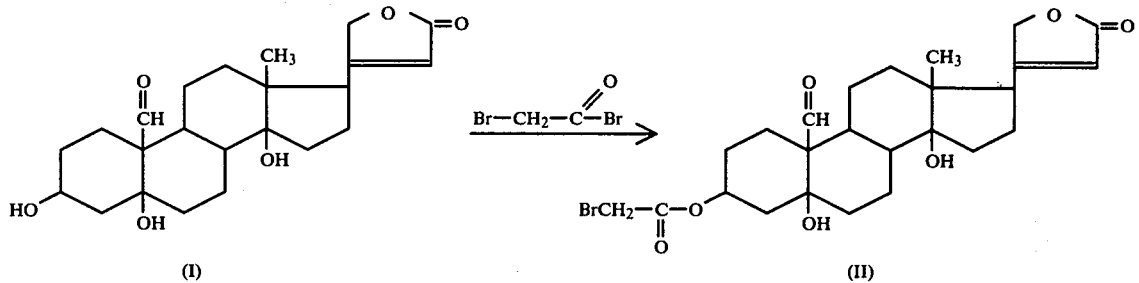

I. Strophanthidin;
   m.p. 144–146°;$[\alpha]_D$=43.2;
   $[M]_D$= +175° (in chloroform-methanol)

II. 3-0-(2¹-bromo)-acetyl-strophanthidin; m.p. 217–219°;
   $[\alpha]_D$= +44.0°;$[M]_D$= +231° (in chloroform-methanol)

When hellebrigenine is used as the original stock, the reaction takes place according to the following pattern:

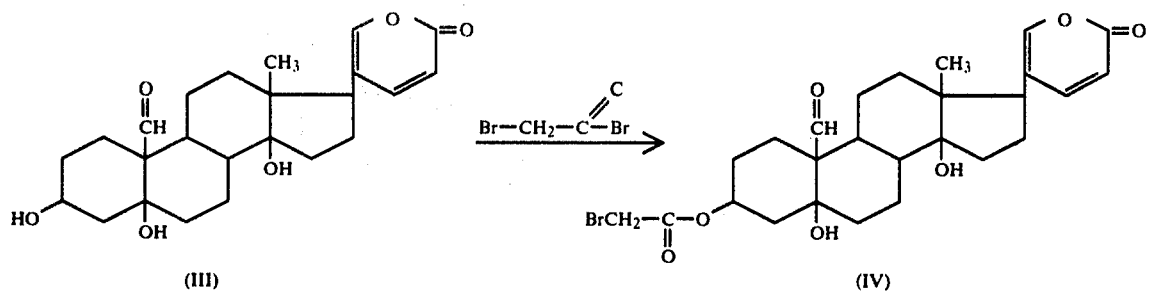

(III)  
III. Hellebrigenine;
  m.p. 150–155°/238–240°;
  $[\alpha]_D = +19.0$ (in chloroform-alcohol); $[M]_D = +79°$ (in chloroform-alcohol)

(IV)  
IV. 3-0-(2¹-bromo)-acetyl-hellebrigenine; m.p. 204–206°; $[\alpha]_D = +30.0°$; $[M]_D = +161°$ (in chloroform)

The reaction is monitored for completeness by means of paper chromatography. Upon the completion of the reaction an excess of ice water is added to crystallize and isolate the halide of cardenolide or bufadienolide which is used in the synthesis reaction that follows. The yield of the intermediate is up to 80 wt.% of theory.

The halide of cardenolide or bufadienolide obtained at the first stage is mixed with an equimolar quantity of ajmaline in a medium of an organic solvent such as acetonitrile, the reaction taking the following course:

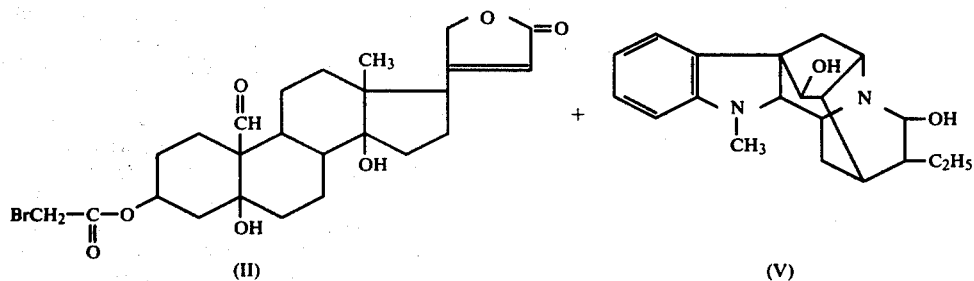

(II)

(V)  
V. Ajmaline; m.p. 158–160°; $[\alpha]_D = +128°$;
  $[M]_D = +417°$ (in a solution of chloroform)

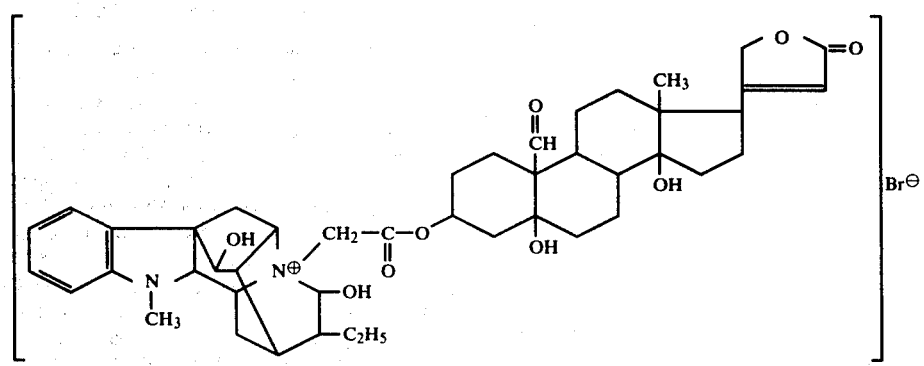

VI. Strophanthidin-3-0-acetyl-2¹N(b)-ajmaline-bromide;
  m.p. 210–212°; $[\alpha]_D = +41.5°$; $[M]_D = +353°$ (in a solution of pyridine)

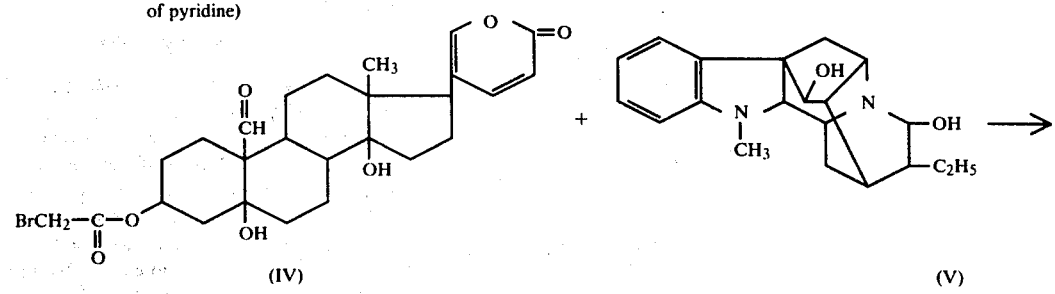

(IV)                                          (V)

-continued

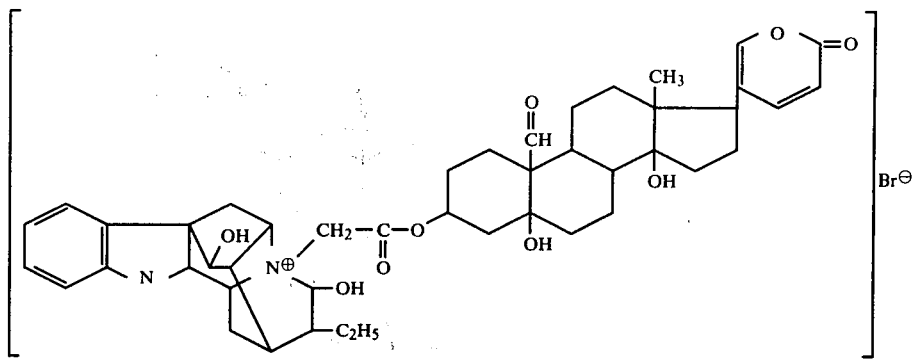

VII. Hellebrigenine-3-0-acetyl-2¹-N(b)-ajmaline-bromide; m.p. 238–241°; $[\alpha]_D = +28.3°$; $[M]_D = +244°$ (in a solution of pyridine)

Upon termination of the reaction which is monitored by means of paper chromatography a two or threefold volume of diethyl ether is added to the reaction mixture. The end product in the form of a crystalline precipitate which is essentially the cardenolide or bufadienolide derivative of ajmaline is isolated and recrystallized. The yield is 70 to 75 wt./ of theory.

For a better understanding of the present invention the following examples of its embodiment are presented below.

EXAMPLE 1

30 g of strophanthidin is dissolved in 60 ml of absolute pyridine.

The solution is cooled to 0° to +3° C. whereupon added thereto at a slow rate (within 10 to 15 minutes) from a separatory funnel is 10 ml (1.7-fold amount of the estimated quantity) monobromo-acetyl-bromide diluted with 45 ml of absolute dioxane. In an hour added to the reaction mixture under stirring is 600 g of ice whereupon the mixture is allowed to stay at 0° to +3° C. for 17 to 20 hours for crystallization. The precipitated crystals are filter-separated, washed with water (100–120 ml) and dissolved in 2 liters of ethanol while heating. Added to the resulting solution is 0.5 g of activated charcoal, the solution is filtered and the filtrate is evaporation-concentrated to about 200 ml. This results in rapid crystallization of bromoacetylstrophanthidin.

The crystals are separated and washed with alcohol. The yield of 3-O-2¹-bromoacetylstrophanthidin is 26 g; m.p. 317°–219° C.; $[\alpha]_D = +44.0° \pm 2°$ (concentration 1.0; the chloroform-methanol ratio, 7:1); $[M]_D = +231° \pm 10°$.

12.5 g of ajmaline and 19.8 g of the thus-obtained bromoacetylstrophanthidin, taken in equimolecular ratios, are dissolved in 190 ml of acetonitrile, and the solution is allowed to stay for 40 hours at room temperature (20° to 22° C.). The reaction terminates within said period, and strophanthidin-3-O-acetyl-2¹-N(b)-ajmaline-bromide precipitates. To make precipitation of the end product more complete, a double volume of diethyl ether is added to the flask with the reaction mixture. The reaction product is separated on a Büchner filter and washed with 50 ml of diethyl ether, filtered, and dissolved in 320 ml of a 96% ethanol, whereupon added thereto at a slow rate (within one hour) is 1.5 l of diethyl ether and the reaction mixture is allowed to stay for 2 hours at room temperature. The crystals are filtration-separated, washed with diethyl ether (208 ml) and air-dried to obtain 22–24 g of strophanthidin-3-O-acetyl-2¹-N(b)-ajmaline-bromide —m.p. 210°–212° C.; $[\alpha]_D = +41.5° \pm 2°$ (concentration 2.00; pyridine); $[M]_D = +353° \pm 17°$. The compound is soluble in alcohol, pyridine, dimethylformamide; sparingly soluble in water; insoluble in ethers and benzene.

IR-spectrum of said compound superposed against a background of the spectrum of ajmaline base is characterized by absorption bands at frequencies of 1,738; 1,700; 1,622 cm⁻¹ and others, characteristic of the strophanthidin component of the molecule, and at frequencies of 1,610; 1,233; 1,200; 760 cm⁻¹ and others characteristic of its ajmaline component. At the same time, the spectrum is devoid of the bands corresponding to valence vibrations at frequencies of 1,053 and 1,040 cm⁻¹, characteristic of the tertiary nitrogen atom; disappearance of such bands is accounted for by the formation of the quaternary ammonium salt which features no characteristic absorption bands. This unambiquously points to strophanthidin being linked through the N(b) atom.

Found,%:N— 3.57; Br—9.51. Calculated,%: N—3.29; Br—9.39.

EXAMPLE 2

Hellebrigenine is acylated with monobromo-acetyl halide in the way similar to that described hereinbefore for strophanthidin to produce the intermediate product, viz., 3-O-(2¹-bromo)-acetylhellebrigenine $C_{26}H_{33}O_7Br$, m.p. 204°–206°; $[\alpha]_D = +30.0°$, and accordingly, $[M]_D = +161°$ in chloroform; R hellebrigenine=2.70 in the system m-xylol-methylethylketone(1:1)-formamide.

The reaction between the intermediate compound 3-O-(2¹-bromo)-acetylhellebrigenine and ajmaline (V) is conducted in the same way as with cardenolides in Example 1 to obtain the end product, viz., hellebrigenine-3-O-acetyl-2¹-N(b)-ajmaline-bromide (VII) $C_{46}H_{59}O_9N_2Br$; m.p. 238°–241° C.; $[\alpha]_D = +28.3°$, and accordingly, $[M]_D = +244°$ in pyridine; R hellebrigenine=1.85 in the same system of solvents as in Example 1.

EXAMPLE 3

10 g of straphanthidin is dissolved in 50 ml of absolute dioxane, 5 ml of triethylamine being added to the reaction solution. Then 3 ml of monochloroacetyl chloride diluted with 10–15 ml of absolute dioxane is added to the reaction mixture while stirring, at a slow rate, within 10 to 15 minutes from a separatory funnel. The solution is allowed to stay for one hour. The reaction is monitored for completeness by means of paper chromatography. Upon termination of the reaction, 300 ml of water is added to the reaction products which are left for crystallization for 18-20 hours.

The crystalline precipitate fallen out is separated on a filter, washed with water, and dissolved in 0.7 l of ethanol under heating; then added thereto is 0.2 g of activated charcoal, and the solution is filtered. The solution is concentrated to about 70 ml by heating in vacuum to 60° C. with the resultant rapid crystallization of chloroacetylstrophanthidin. The crystals are separated by filtration and washed with ethanol to yield 9 g of 3-O-(2¹-chloro)-acetylstrophanthidin with a melting point of 225°-234° C., $[\alpha]_D = +48 \pm 2°$ (concentration 1.0; pyridine); molecular formula $C_{25}H_{33}O_7Cl$, molecular weight 481.0.

Thereupon 5 g of 3-O-(2¹-chloro)-acetylstrophanthidin and 3.4 g of ajmaline are dissolved in 50 ml of acetonitrile, and the solution is left for 70 hours at room temperature (20°-25° C.). Then a two-fold volume of diethyl ether is added to the reaction mixture. The resulting precipitate is filtered off and washed with ether (20 ml) to obtain 6.7 g of strophanthidin-3-O-acetyl-2¹-N(b)ajmaline-chloride; molecular formula $C_{45}H_{59}O_9N_2Cl$; molecular weight 807.5; $[\alpha]_D = +43° \pm 2°$ (concentration 1.0; pyridine); $[M]_D = +347° \pm 16°$ (in pyridine); m.p. 250°-253°.

EXAMPLE 4

17β-H-strophanthidin is reacted with monobromoacetyl halide observing the conditions described in Example 1. The thus-obtained intermediate 3-O-(2-bromo)-acetyl-17β-H-strophanthidin is used in the reaction with ajmaline, also observing the conditions of Example 1, to yield 17β-H-strophanthidin-3-O-acetyl-2¹-N(b)-ajmaline-bromide with a molecular formula $C_{45}H_{59}O_9N_2Br$, m.p. 217°-220°; $[\alpha]_D = +36.1° \pm 2°$ (concentration 1.00; pyridine) and 71.1°±3° (concentration 1.00; ethanol); $[M]_D = +605.8° \pm 27°$.

Found, wt.%: N—3.34; Br—9.26. Calculated, wt.%: N—3.29; Br—9.39.

EXAMPLE 5

Digitoxigenin is reacted with monobromo-acetyl halide under the conditions described in Example 1 to obtain an intermediate compound, viz., 3-O-(2-bromo)-acetyl-digitoxigenin.

The reaction between the intermediate compound 3-O-(2-bromo)-acetyl-digitoxigenin and ajmaline (V) in the same manner as in Example 1 to obtain the end product, viz., digitoxigenin-3-O-acetyl-2¹-N(b)-ajmaline-bromide, with a molecular formula $C_{45}H_{61}O_7N_2Br$, m.p. 215°-218°; $[\alpha]_D = +58.0 \pm 3.0$ (concentration 1.00; in a solution of ethanol); $[M]_D = +477° \pm 24°$ (in a solution of ethanol).

What we claim is:

1. The cardenolide and bufadienolide derivatives of ajmaline of the formula

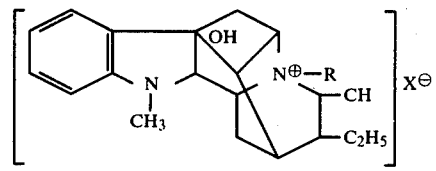

wherein

R is a steroid radical selected from the group consisting of cardenolide and bufadienolide of the formula

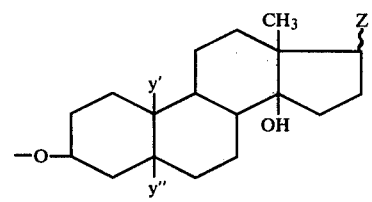

wherein

Z is an unsaturated lactone ring selected from the group consisting of a five-member unsaturated lactone ring of the formula

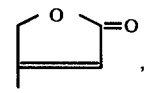

a six-member unsaturated lactone ring of the formula

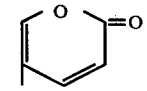

y' is a radical selected from the group consisting of —CH₃, —CHO; y" is a substituent selected from the group consisting of hydrogen and a hydroxy group;

X is a halogen radical.

2. Strophanthidin-3-O-acetyl-2¹-N(b)-ajmaline-bromide of the formula as claimed in claim 1:

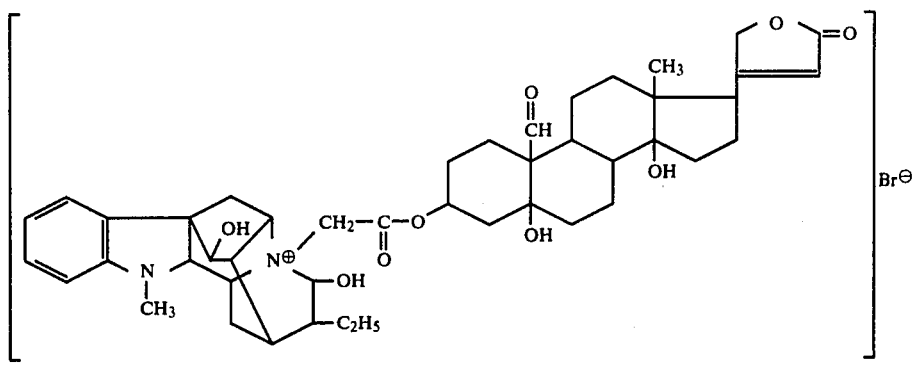
3. Hellebrigenine-3-O-acetyl-2¹-N(b)-ajmaline-bromide of the formula as claimed in claim 1:
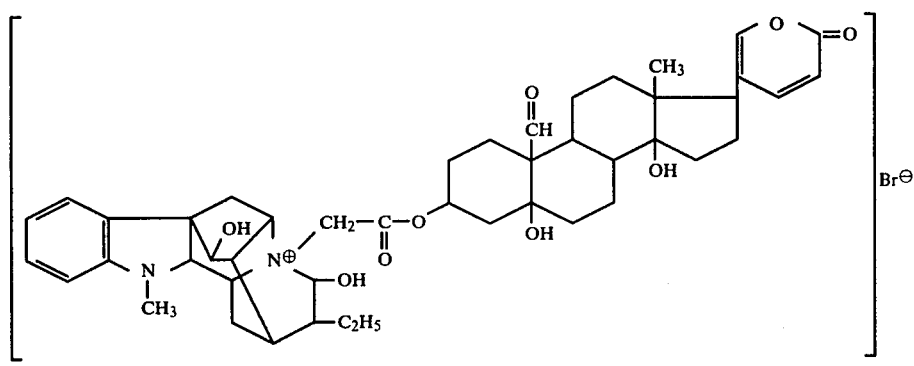
4. 17β-H-Strophanthidin-3-O-acetyl-2¹-N(b)-ajmaline-bromide as claimed in claim 1:
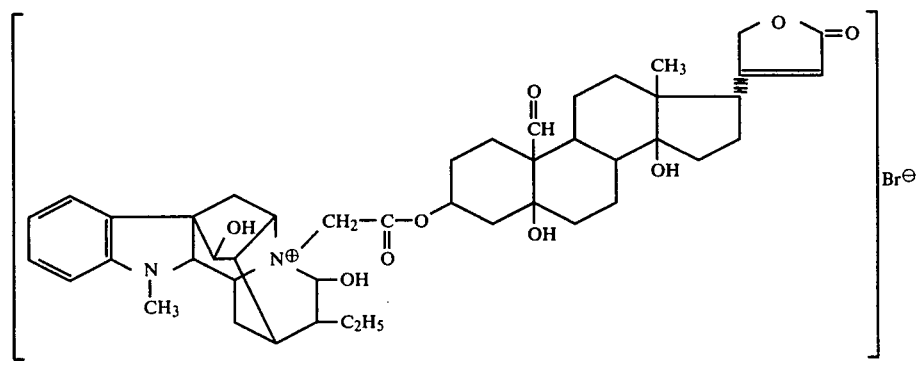
5. Digitoxigenin-3-O-acetyl-2¹-N(b)-ajmaline-bromide as claimed in claim 1:

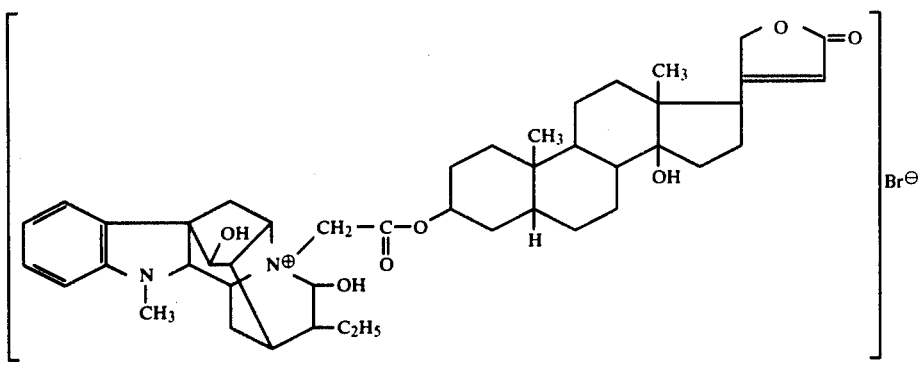

6. Strophanthidin-3-O-acetyl-2¹-N(b)-ajmaline-chloride as claimed in claim 1:

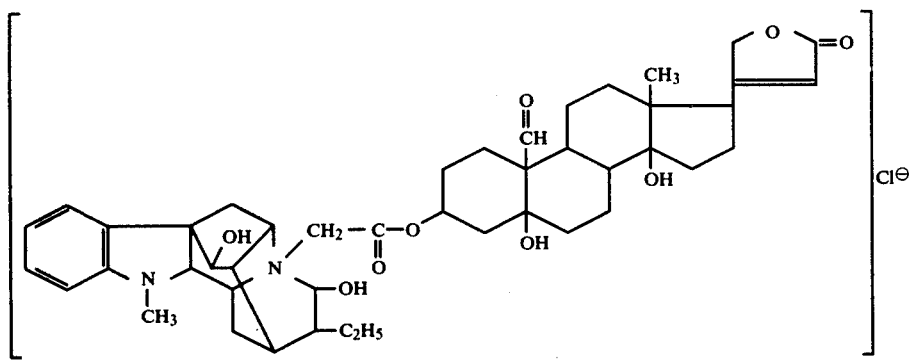

7. A process for producing the cardenolide and bufadienolide derivatives of ajmaline of the formula

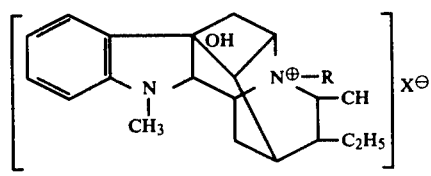

wherein

R is a steroid compound selected from the group consisting of cardenolide and bufadienolide of the formula

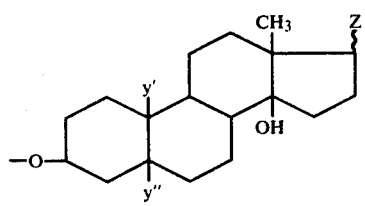

Z is an unsaturated lactone ring selected from the group consisting of a five-member unsaturated lactone ring of the formula

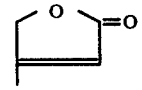

a six-member unsaturated lactone ring of the formula

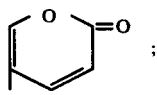

$y'$ is a radical selected from the group consisting of $CH_3$, $-CHO$, $y''$ is a substituent selected from the group consisting of hydrogen, and a hydroxy group;

X is a halogen radical, which comprises reacting said steroid compound selected from the group consisting of cardenolide and bufadienolide with an acid halide in a medium of an organic solvent, which is unreactive with organic acid anhydrides, at a temperature of $-10°$ to $+25°$ C., and adding ajmaline to the thus-obtained halide of said steroid compound in a medium of said organic solvent, followed by isolation of the end product.

* * * * *